United States Patent

Pissiotas et al.

[11] 3,941,829
[45] Mar. 2, 1976

[54] N-PHENYL-N'-CARBOPHENOXY FORMAMIDINES

[75] Inventors: Georg Pissiotas, Lorrach, Germany; Dieter Dürr, Bottmingen, Switzerland

[73] Assignee: Ciba-Geigy Corporation, Ardsley, N.Y.

[22] Filed: Dec. 1, 1972

[21] Appl. No.: 311,058

[30] Foreign Application Priority Data

| Dec. 7, 1971 | Switzerland | 17790/71 |
| Dec. 7, 1971 | Switzerland | 17791/71 |
| Jan. 26, 1972 | Switzerland | 1224/72 |
| Oct. 27, 1972 | Switzerland | 15729/72 |

[52] U.S. Cl....... 260/471 C; 260/240 G; 260/465 D; 260/470; 260/472; 424/277; 424/278; 424/285; 424/300
[51] Int. Cl.²........................... C07C 125/06
[58] Field of Search..... 260/471 C, 472, 470, 240 G

[56] References Cited
FOREIGN PATENTS OR APPLICATIONS

| 890,922 | 1/1972 | Canada |
| 2,202,034 | 1/1972 | Germany |
| 2,123,001 | 8/1972 | France |
| 778,383 | 7/1972 | Belgium |

*Primary Examiner*—Anton H. Sutto
*Assistant Examiner*—Michael Shippen
*Attorney, Agent, or Firm*—Harry Falber; Frederick H. Rabin; Philip P. Berestecki

[57] ABSTRACT

Phenylformamidines of the formula

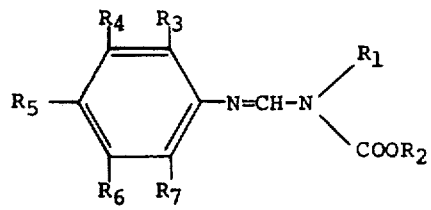

wherein $R_1$ represents hydrogen, alkyl, alkenyl or alkynyl, $R_2$ represents α-naphthyl,

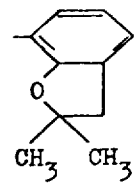

or substituted phenyl,
wherein the phenyl group is not substituted simultaneously in the 2-position by a methyl group and in the 4-position by a chlorine atom, $R_3$, $R_4$, $R_5$, $R_6$ and $R_7$ represent one or more radicals which are the same or different, such as hydrogen or halogen atoms or alkyl, alkoxy, alkylthio, alkenyloxy, alkynyloxy, alkoxycarbonyl, $CF_3$, cyano or nitro groups, their process for the manufacture and their use in pest control.

6 Claims, No Drawings

N-PHENYL-N'-CARBOPHENOXY FORMAMIDINES

The present invention relates to phenylformamidines, a process for their manufacture and their use in pest control.

The phenyformamidines have the formula

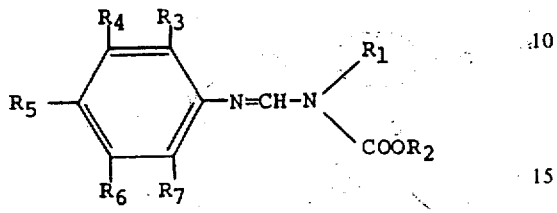

wherein $R_1$ represents hydrogen, alkyl, alkenyl or alkynyl, $R_2$ represents α-naphthyl,

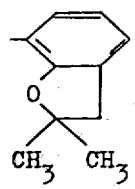

or substituted phenyl,
wherein the phenyl group is not substituted simultaneously in the 2-position by a methyl group and in the 4-position by a chlorine atom, $R_3$, $R_4$, $R_5$, $R_6$ and $R_7$ represent one or more radicals which are the same or different, such as hydrogen or halogen atoms or alkyl, alkoxy, alkylthio, alkenyloxy, alkynyloxy, alkoxycarbonyl, $CF_3$, cyano or nitro groups.

The alkyl, alkyloxy, alkylthio, alkenyl, alkenyloxy, alkynyl or alkynyloxy groups represented by $R_1$ and $R_3$, $R_4$, $R_5$, $R_6$ and $R_7$ contain 1 to 18, preferably 1 to 4, carbon atoms in the chain; the alkenyl and alkynyl chains contain 3 to 18, preferably 3 to 5, carbon atoms. These groups may be straight-chain or branched, substituted or unsubstituted. Possible substituents are halogen atoms. By halogen is meant fluorine, chlorine, bromine and/or iodine. Examples of such groups include: methyl, methoxy, methylthio, ethyl, ethoxy, trifluoromethyl, chloroethyl, propyl, isopropyl, n-, i-, sec. and tert. butyl, allyl, methallyl, propargyl, n-butynyl, isobutynyl.

Possible substituents at the phenyl group represented by $R_2$ are chiefly one or more similar or different halogen atoms, such as fluorine, chlorine, bromine and/or iodine and/or alkyl with 1 to 5 carbon atoms, haloalkyl with 1 to 4 carbon atoms, alkoxy with 1 to 4 carbon atoms, alkoxyalkyl with 1 to 4 carbon atoms in each of the moieties, alkylthio with 1 to 4 carbon atoms, alkynyloxy with 3 to 4 carbon atoms, dialkylamino with 1 to 4 carbon atoms, dialkenylamino, dialkynylamino, N-alkyl-N-alknylamino, N-alkyl-N-alkenylamino, HO, NC and/or $O_2N$ groups, as well as cyclopentyl, monoalkylaminomethyleneimino, dialkylaminomethyleneimino, cyclopentyl

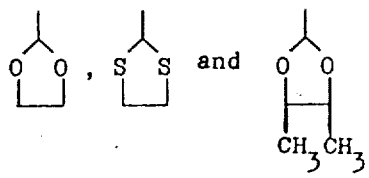

groups.

Preferred compounds on account of their action are those of the formula I, wherein $R_1$ represents methyl, $R_2$ represents α-naphthyl,

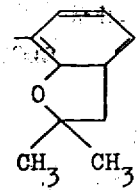

2-methylphenyl, 3-methylphenyl, 2-chlorophenyl, 2-isopropylphenyl, 3-isopropylphenyl, 3-methyl-5-isopropylphenyl, 2-chloro-5-tert.butylphenyl, 3,4-dimethylphenyl, 3,4,5-trimethylphenyl, 3,5-dimethyl-4-methyltiophenyl, 3,5-di-tert.butylphenyl, 2-isopropoxyphenyl, 2-allyloxyphenyl, 3-methyl-4-dimethylaminophenyl, 3,5-dimethyl-4-dimethylaminophenyl, 3,5-dimethyl-4-diallylaminophenyl, 1,3-dioxolan-2-yl-phenyl, 1,3,-diothiolan-2-yl-phenyl, (4,5-dimethyl-1,3-dioxolan-2-yl)-phenyl, 3-(1-methylbutyl)-phenyl, 2-sec.butylphenyl, 3-(1-ethylpropyl)-phenyl, 2,3-xylyl, 3-tert.butylphenyl, 3-sec.butylphenyl, 3,5-diisopropylphenyl, 2-chloro-5-isopropylphenyl, 3,5-dimethyl-4-methoxyphenyl, 3-allyloxyphenyl, 2-propargyloxymethoxyphenyl, 2-Y-methylthiopropylphenyl, 3-(α-methoxymethyl)-2-propenylphenyl, 4-(methyl-propargylamino)-3,5-xylyl, 4-(methyl-Y-chloroallylamino)-3,5-xylyl, 2-(ethyl-propargylamino)phenyl, 2-chloro-4,5-dimethylphenyl, 2-(2-propynyloxy)-phenyl, 3-(2-propynyloxy)-phenyl, 2-dimethylaminophenyl, 2-diallylaminophenyl, 3-methyl-4-dimethylaminomethyleneiminophenyl, 3-dimethylaminomethyleneiminophenyl, 3-isopropyl-4-methylthiophenyl, 5,6,7,8-tetrahydronaphthyl, 2-(methyl-propargylamino)-phenyl, 2-(dipropargylamino)-phenyl, 4-(dipropargylamino)-3-tolyl, 4-(dipropargylamino)-3,5-xylyl, 2-(allyl-isopropylamino)-phenyl, 3-(allyl-isopropylamino)-phenyl, 3-methoxymethoxy-phenyl, 2-cyclopentylphenyl, 2-(1-butyn-3-yl-oxy)phenyl or 2-(1-methoxy-2-propoxy)-phenyl, $R_3$, $R_4$, $R_5$, $R_6$ and $R_7$ represent radicals which are the same or different, such as hydrogen, fluorine, chlorine and/or bromine atoms, or methyl, methoxy, methylthio, trifluoromethyl, ethoxycarbonyl, ethylpropyl, isopropyl, n-butyl, allyloxy, propargyloxy, NC or $O_2N$ groups, and $n$ is 1 to 3.

Examples of suitable compounds of the formula I include:

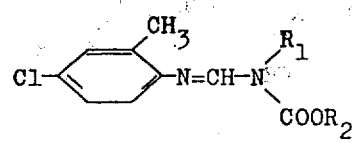

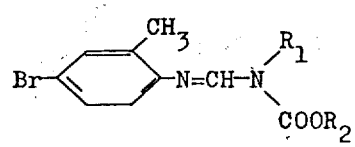

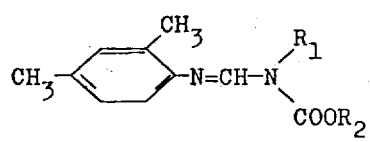

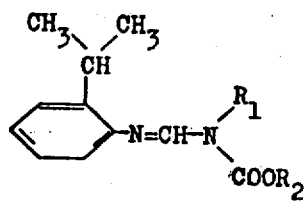
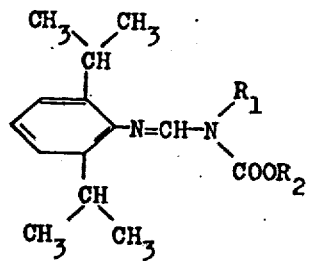
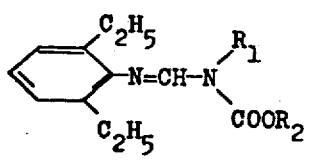
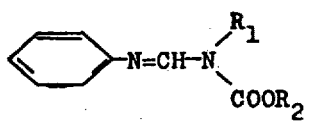
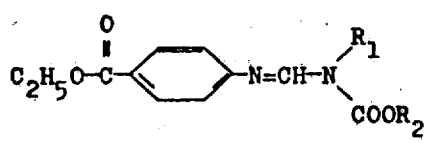
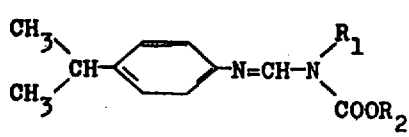
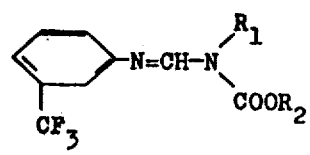
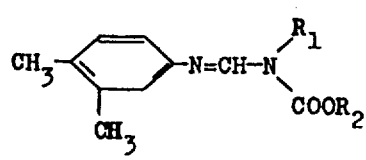
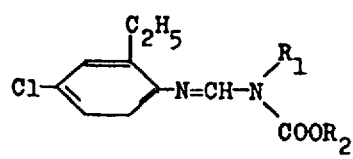
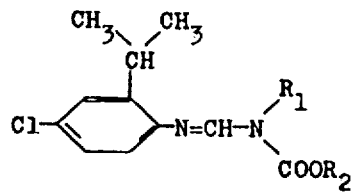
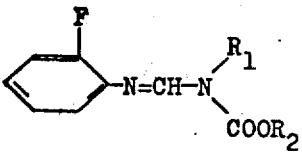
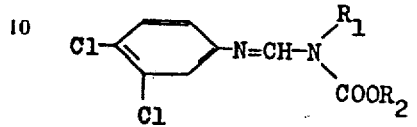
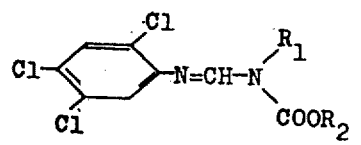
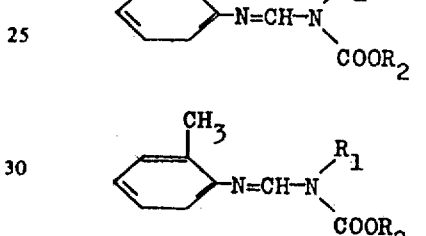
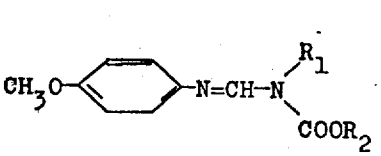
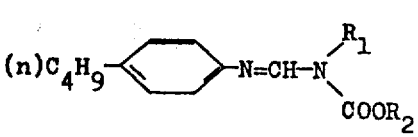
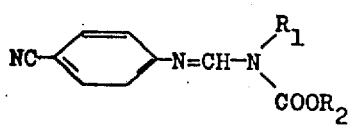
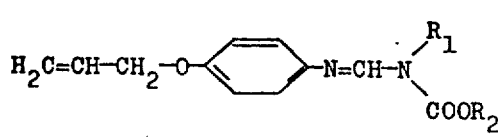
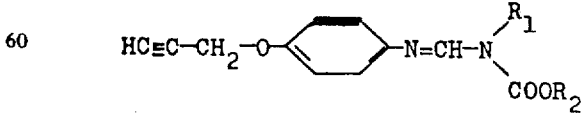
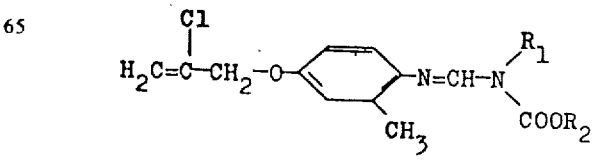

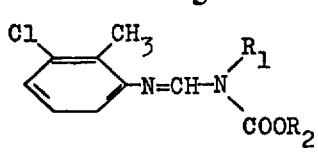

wherein R₁ represents alkyl with 1 to 12 carbon atoms, allyl or propargyl, and R₂ represents α-naphthyl,

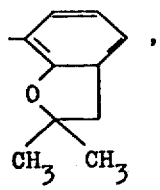

2-methylphenyl, 3-methylphenyl, 2-chlorophenyl, 2-isopropylphenyl, 3-isopropylphenyl, 3-methyl-5-isopropylphenyl, 2-chloro-5-tert.butylphenyl, 3,4-dimethylphenyl, 3,4,5-trimethylphenyl, 3,5-dimethyl-4-methylthiophenyl, 3,5-di-tert.butylphenyl, 2-isopropoxyphenyl, 2-allyloxyphenyl, 3-methyl-4-dimethylaminophenyl, 3,5-dimethyl-4dimethylaminophenyl, 3,5-dimethyl-4-diallylaminophenyl, 1,3-dioxolan-2-yl-phenyl, 1,3-dithiolan-2-yl-phenyl, (4,5-dimethyl-1,3-dioxolan-2-yl)-phenyl, 3-(1-methylbutyl)-phenyl, 2-sec.butylphenyl, 3-(1-ethylpropyl)-phenyl, 2,3-xylyl, 3-tert.butylphenyl, 3-sec.butylphenyl, 3,5-diisopropylphenyl, 2-chloro-5-isopropylphenyl, 3,5-dimethyl-4-methoxyphenyl, 3-allyloxyphenyl, 2-propargyloxymethoxyphenyl, 2-Y-methylthiopropylphenyl, 3-(α-methoxymethyl)-2-propenylphenyl, 4-(methyl-propargylamino)-3,5-xylyl, 4-(methyl-Y-chloroallylamino)-3,5-xylyl, 2-(ethyl-propargylamino)phenyl, 2-chloro-4,5-dimethylphenyl, 2-(2-propynyloxy)-phenyl, 3-(2-propynyloxy)-phenyl, 2-dimethylaminophenyl, 2-diallylaminophenyl, 3-methyl-4-dimethylaminomethyleneiminophenyl, 3-dimethylaminomethyleneiminophenyl, 3-isopropyl-4-methylthiophenyl, 5,6,7,8-tetrahydronaphthyl, 2-(methyl-propargylamino)-phenyl, 2-(dipropargylamino)-phenyl, 4-(dipropargylamino)-3-tolyl, 4-(dipropargylamino)-3,5-xylyl, 2-(allyl-isopropylamino)-phenyl, 3-(allyl-isopropylamino)-phenyl, 3-methoxymethoxy-phenyl, 2-cyclopentylphenyl, 2-(1-butyn-3-yl-oxy)phenyl or 2-(1-methoxy-2-propoxy)-phenyl.

The compounds of the formula I can be manufactured by methods which are known per se, e.g. by reacting formamidines of the formula

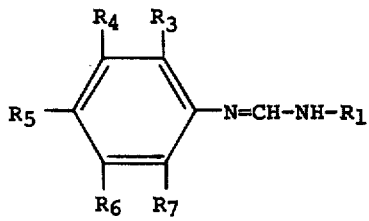

with a chloroformic ester of the formula

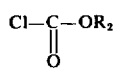 (III)

in the presence of an acid binding agent. In the formulae II and III, R₁ to R₇ have the same meanings as given for the formula I.

Examples of suitable acid binding agents are: formamidines of the formula II; tertiary amines, such as triethylamine, dimethylaniline, pyridine, inorganic bases, such as hydroxides and carbonates of alkali and alkaline earth metals, preferably sodium and potassium carbonate.

The reaction is carried out preferably in solvents or diluents which are inert towards the reactants. Examples of suitable solvents or diluents are: aromatic hydrocarbons, such as benzene, toluene, benzines, halogenated hydrocarbone, chlorobenzene, polychlorobenzenes, bromobenzene, chlorinated alkanes with 1 to 3 carbon atoms; ethers, such as dioxan, tetrahydrofuran; esters, such as ethyl acetate; ketones, such as methyl ethyl ketone, diethyl ketone, nitriles etc.

Some of the starting materials of the formula II and III are known compounds which can be manufactured by methods which are known per se. The compounds of the formula I display a broad biocidal activity and can be used for combating diverse plant and animal pests.

In particular, however, they possess insecticidal and acaricidal properties and may be used against all development states, e.g. eggs, larvae, pupae, nymphs and adults, of insects and representatives of the order Acarina, for example against insects of the families:

| | |
|---|---|
| *Tettigoniida* | *Tenebrionidae* |
| *Gryllidae* | *Chrysomelidae* |
| *Gryllotalpidae* | *Bruchidae* |
| *Blattidae* | *Tineidae* |
| *Reduviidae* | *Noctuidae* |
| *Phyrrhocoridae* | *Lymatriidae* |
| *Cimicidae* | *Pyralidae* |
| *Delphacidae* | *Culicidae* |
| *Aphididae* | *Tipulidae* |
| *Diaspididae* | *Stomoxydae* |
| *Pseudococcidae* | *Trypetidae* |
| *Scarabacidae* | *Muscidae* |
| *Dermestidae* | *Calliphoridae* and |
| *Coccinellidae* | *Pulicidae* |

Acarida of the families:
Ixodidae
Argasidae
Tetranychidae and
Dermanyssidae.

The insecticidal and/or acaricidal action can be substantially broadened and adapted to suit the particular circumstances by the addition of other insecticides and/or acaricides, among such other insecticides and acaricides are included the following.

Organic phosphorus compounds

Bis-O,O-diethylphosphoric acid anhydride (TEPP)
Dimethyl-(2,2,2-trichloro-1-hydroxyethyl)-phosphonate TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)

3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
0,0-diethyl-0(or S)-2-(ethylthio)-ethylthiophosphate (DEMETON)
S-ethylthioethyl-0,0-dimethyl-dithiophosphate (THIOMETON)
0,0-diethyl-S-ethylmercaptomethyldithiophosphate (PHORATE)
0,0-diethyl-S-2-(ethylthio)ethyidithiophosphate (DISULFOTON)
0,0-dimethyl-S-2-(ethylsulphinyl)ethylthiophosphate (OXYDEMETON METHYL)
0,0-dimethyl-S-(1,2-dicarbethoxyethyldithiophosphate (MALATHION)
0,0,0,0-tetraethyl-S,S'-methylene-bis-dithiophosphate (ETHION)
0-ethyl-S,S-dipropyldithiophosphate
0,0-dimethyl-S-(N-methyl-N-formylcarbamoylmethyl)-dithiophosphate (FORMOTHION)
0,0-dimethyl-S-(N-methylcarbamoylmethyl)dithiophosphate (DIMETHOATE)
0,0-dimethyl-0-p-nitrophenylthiophosphate (PARATHION-METHYL)
0,0-diethyl-0-p-nitrophenylthiophosphate (PARATHION)
0-ethyl-O-p-nitrophenylphenylthiophosphate (EPN)
0,0-dimethyl-0-(4-nitro-m-tolyl)thiophosphate (FENITROTHION)
0,0-dimethyl-0-2,4,5-trichlorophenylthiophosphate (RONNEL)
0-ethyl-0,2,4,5-trichlorophenylethylthiophosphate (TRICHLORONATE)
0,0-dimethyl-0-2,5-dichloro-4-bromophenylthiophosphate (BROMOPHOS)
0,0-dimethyl-0-(2,5-dichloro-4-iodophenyl)-thiophosphate (JODOFENPHOS)
4-tert.butyl-2-chlorophenyl-N-methyl-0-methylamidophosphate (CRUFOMATE)
0,0-dimethyl-0-(3-methyl-4-methylmercaptophenyl)thiophosphate (FENTHION)
Isopropylamino-O-ethyl-O-(4-methylmercapto-3-methylphenyl)phosphate
0,0-diethyl--0-p-(methylsulphinyl)phenyl-thiophosphate (FENSULFOTHION)
0-p-(dimethylsulphamido)phenyl-0,0-dimethylthiophosphate (FAMPHUR)
0,0,0',0'-tetramethyl-0,0'-thiodi-p-phenylenethiophosphate
0-ethyl-S-phenyl-ethylthiophosphate
0,0-dimethyl-0-(-methylbenzyl-3-hydroxycrotonyl)-phosphate
2-chloro-1-(2,4-dichlorophenyl)vinyl-diethylphosphate CHLORFENVINPHOS) 1-chloro-1-(2,4,5-trichlorophenyl)vinyl-dimethylphosphate
0-[2-chloro-1-(2,5-dichlorophenyl)]vinyl-0,0-diethylthiophosphate
Phenylglyoxylonitriloxime-0,0-diethylthiophosphate (PHOXIM)
0,0-diethyl-O-(3-chloro-4-methyl-2-oxo-2-H-1-benzopyran-7-yl)thiophosphate (COUMAPHOS)
2,3-p-dioxandithiol-S,S-bis(0,0-diethyldithiophosphate) (DIOXATHION)
5-[(6-chloro-2-oxo-3-benzoxazolinyl)methyl]0,0-diethyldithiophosphate (PHOSALONE)
2-(diethoxyphosphinylimino)-1,3-dithiolane
0,0-dimethyl-S-[2-methoxy-1,3,4-thiadiazol-5-(4H)-onyl-(4)methyl]dithiophosphate
0,0-dimethyl-S-phthalimidomethyl-dithiophosphate (IMIDAN)
0,0-diethyl-0-(3,5,6-trichloro-2-pyridyl)thiophosphate
0,0-diethyl-0-2-pyrazinylthiophosphate (THIONAZIN)
0,0-diethyl-0-(2-isopropyl-4-methyl-6-pyrimidyl)thiophosphate (DIAZINON)
0,0-diethyl-0-(2-quinoxalyl)thiosphosphate
0,0-dimethyl-S-(4-oxo-1,2,3-benzotriazin-3-(4H)-ylmethyl)dithiophosphate (AZINPHOSMETHYL)
0,0-diethyl-S-(4-oxo-1,2,3-benzotriazin-3-(4H)-ylmethyl)dithiophosphate (AZINPHOSETHYL)
S-[(4,6-diamino-s-triazin-2-yl)methyl]-0,0-dimethyldithiophosphate (MENAZON)
0,0-dimethyl-0-(3-chloro-4-nitrophenyl)thiophosphate (CHLORTHION)
0,0-dimethyl-0(or S)-2-(ethylthioethyl)thiophosphate (DEMETON-S-METHYL)
2-(0,0-dimethyl-phosphoryl-thiomethyl)-5-methoxypyrone-4-3,4-dichlorobenzyl-triphenylphosphoniumchloride
0,0-diethyl-S-(2,5-dichlorophenylthiomethyl)dithiophosphate (PHENKAPTON)
0,0-diethyl-0-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(0,0-dimethylthiolphosphoryl)-3-thiavaleramide (VAMIDOTHION)
0,0-diethyl-0-[2-dimethylamino-4-methylpyrimidyl-(6)]-thiophosphate (DIOCTHYL)
0,0-dimethyl-S-(methylcarbamoylmethyl)-thiophosphate (OMETHOATE)
0-ethyl-0-(8-quinolinyl)-phenylthiophosphonate (OXINOTHIOPHOS)
0-methyl-S-methyl-amidothiophosphate (MONITOR)
0-methyl-0-(2,5-dichloro-4-bromophenyl)-benzothiophosphate (PHOSVEL)
0,0,0,0-tetrapropyldithiophosphate
3-(dimethoxyphosphinyloxy)-N-methyl-N-methoxy-cis-crotonamide
0,0-dimethyl-S-(N-ethylcarbamoylmethyl)dithiophosphate (ETHOATE-METHYL)
0,0-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-0,0-dimethyldithiophosphate
Hexamethylphosphoric acid triamide (HEMPA)
0,0-dimethyl-0-(2-chloro-4-nitrophenyl)thiophosphate (DICAPTHON)
0,0-dimethyl-0-p-cyanophenyl thiophosphate (CYANOX)
0-ethyl-0-p-cyanophenylthiophosphonate
0,0-diethyl-0-2,4-dichlorophenylthiophosphate (DICHLORFENTHION)
0,2,4-dichlorophenyl-0-methylisopropylamidothiophosphate 0,0-diethyl-0-2,5-dichloro-4-bromophenylthiophosphate (BROMOPHOS-ETHYL)
dimethyl-p-(methylthio)phenylphosphate
0,0-dimethyl-0-p-sulphamidophenylthiophosphate
0-[p-(p-chlorophenyl)azophenyl]0,0-dimethylthiophosphate (AZOTHOATE)
0-ethyl-S-4-chlorophenyl-ethyldithiophosphate
0-isobutyl-S-p-chlorophenyl-ethyldithiophosphate
0,0-dimethyl-S-p-chlorophenylthiophosphate
0,0-dimethyl-S-(p-chlorophenylthiomethyl)dithiophosphate
0,0-diethyl-p-chlorophenylmercaptomethyl-dithiophosphate (CARBOPHENOTHION)
0,0-diethyl-S-p-chlorophenylthiomethyl-thiophosphate
0,0-dimethyl-S-(carbethoxy-phenylmethyl)dithiophosphate (PHENTHOATE)
0,0-diethyl-S-(carbofluorethoxy-phenylmethyl)-dithiophosphate
0,0-dimethyl-S-carboisopropoxy-phenylmethyl)-dithiophosphate
0,0-diethyl-7-hydroxy-3,4-tetramethylene-coumarinyl-thiophosphate (COUMITHOATE)
2-methoxy-4-H-1,3,2-benzodioxaphosphorin-2-sulphide
0,0-diethyl-0-(5-phenyl-3-isooxazolyl)thiophosphate
2-(diethoxyphosphinylimino)-4-methyl-1,3-dithiolane tris-(2-methyl-1-aziridinyl)-phosphine oxide (METEPA)
S-(2-chloro-1-phthalimidoethyl)-0,0-diethyldithiophosphate
N-hydroxynaphthalimido-diethylphosphate
dimethyl-3,5,6-trichloro-2-pyridylphosphate
0,0-dimethyl-0-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-0,0-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
0,0-dimethyl-0-(2,2-dichloro-1-methoxy-vinyl)phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
0,0-diethyl-0-(2,2-dichloro-1-chloroethoxyvinyl)-phosphate
0,0-dimethyl-0-(2,2-dichloro-1-chloroethoxyvinyl)-phosphate
0-ethyl-S,S-diphenyldithiolphosphate
0-ethyl-S-benzyl-phenyldithiophosphonate
0,0-diethyl-S-benzyl-thiolphosphate
0,0-dimethyl-S-(4-chlorophenylthiomethyl)dithiophosphate (METHYLCARBOPHENOTHION)
0,0-dimethyl-S-(ethylthiomethyl)dithiophosphate
diisopropylaminofluorophosphate (MIPAFOX)
0,0-dimethyl-S-(morpholinylcarbamoylmethyl)dithiophosphate (MORPHOTHION)
bismethylamido-phenylphosphate
0,0-dimethyl-S-(benzenesulphonyl)dithiophosphate
0,0-dimethyl-(S and 0)-ethylsulphinylethylthiophosphate
0,0-diethyl-0-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
0-phenyl-0-p-nitrophenyl-methanethiophosphonate (COLEP)
0-methyl-0-(2-chloro-4-tert.butyl-phenyl)-N-methylamidothiophosphate (NARLENE)
0-ethyl-0-(2,4-dichlorophenyl)-phenylthiophosphonate
0,0-diethyl-0-(4-methylmercapto-3,5-dimethylphenyl)-thiophosphate
4,4'-bis-(0,0-dimethylthiophosphoryloxy)-diphenyl disulphide
0,0-di-(β-chloroethyl)-0-(3-chloro-4-methyl-coumarinyl-7)phosphate
S-(1-phthalimidoethyl)-0,0-diethyldithiophosphate
0,0-dimethyl-0-(3-chloro-4-diethylsulphamylphenyl)-thiophosphate
0-methyl-0-(2-carbisopropoxyphenyl)-amidothiophosphate
5-(0,0-dimethylphosphoryl)-6-chloro-bicyclo(3.2.0)-heptadiene(1,5)
0-methyl-0-(2-i-propoxycarbonyl-1-methylvinyl)-ethylamidothiophosphate.

Nitrophenols and derivatives 4,6-dinitro-6-methylphenol, sodium salt [Dinitrocresol] dinitrobutylphenol-(2,2',2'')-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethrin I
pyrethrin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)

(l)-3-(2-furfuryl)-2-methyl-4-oxocyclopent-2-enyl-(l)-(cis+trans)chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethylbenzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-0-(methylcarbamoyl)-oxime 1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-0-(methylcarbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-0-methylcarbamyl-formoxime
1-(2'-cyanoethylthio)-0-methylcarbamyl-acetaldoxime
1-methylthio-0-carbamyl-acetaldoxime
0-(3-sec.butylphenyl)-N-phenylthio-N-methylcarbamate
2,5-dimethyl-1,3-dithiolane-2-(0-methylcarbamyl)-aldoxime)
0-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethylcarbamate 0-(2,2-dimethyl-4-chloro-2,3-dihydro-7-benzofuranyl)-N-methylcarbamate
0-(2,2,4-trimethyl-2,3-dihydro-7-benzofuranyl)-N-methylcarbamate
0-naphthyl-N-methyl-N-acetal-carbamate
0-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]
1,2,4,5,6,7,8,8-octachloro-3α,4,7,7α'tetrahydro-4,7-methylene indane [CHLORDAN]
1,4,5,6,7,8,8-heptachloro,3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octahydro-exo-1,4,endo-5,8-dimethanonaphthalene [DIFLORIN]
1,2,3,4,10,10-hexachloro-5,7-epoxy-1,4,4α,5,6,7,8,8α-octyhydro-endo-endo-5,8-dimethanonaphthalene [ENDRIN]

The active substances of the formula I are also suitable for combating representatives of the division Thallophyta, e.g. viruses, bacteria and fungi. They thus possess fungicidal properties against phytopathogenic fungi on various cultivated plants, such as cereals, maize, rice, vegetables, ornamental plants, fruit trees, vines, farm products, etc.

With the new active substances it is possible to control or destroy fungi occurring on fruit, blossom, leaves, stems, tubers and roots, and from which parts of plants which grow later then also remain free. The active substances of the formula I are active in particular against phytopathogenic fungi belonging to the following classes:

Oomycetes, Zygomycetes, Ascomycetes, Basidiomycetes, Denteromycetes.

In addition, the new active substances can also be used for treating seeds, fruit, tubers etc., and protecting them from fungus infections, for example from smut fungi of all kinds, such as Ustilaginales, e.g. Ustilago, Tilletia, Urocystis, Turbicinia and Phoma types.

In addition to the above cited acaricides and insecticides, it is also possible to admix the active substances of the formula I with, for example, bactericides, fungistatic agents, bacteriostatic agents, nematocides and/or e.g. the following fungicides, in order to broaden the activity spectrum:

dodecylguanidine acetate (DODINE)
pentachloronitrobenzene (QUINTOZENE)
pentachlorophenol (PCP)
2-(1-methyl-n-propyl)-4,6-dinitrophenyl-2-methylcrotonate (BINAPACRYL)
2-(1-methyl-n-heptyl)-4,6-dinitrophenylcrotonate (DINOCAP)
2,6-dichloro-4-nitroaniline (DICHLORAN)
2,3,5,6-tetrachloro-benzoquinone (1,4) (CHLORANIL)
2,3-dichloro-naphthoquinone (1,4) (DICHLONE)
N-(trichloromethylthio) phthalimide (FOLPAT)
N-(trichloromethylthio) cyclohex-4-ene-1,2-dicarboximide (CAPTAN)
N-(1,1,2,2-tetrachloroethylthio)cyclohex-4-ene-1,2-dicarboximide (CAPTAFOL)
N-methansulfonal-N-trichloromethylthio-chloroaniline
N'-dichlorofluoromethylthio-N,N-dimethyl-N'-phenylsulphamide (DICHLOFLUANID)
0-ethyl-S-benzyl-phenyldithiophosphate
0,0-diethyl-S-benzyl-thiolphosphate
disodium-ethylene-1,2-bis-dithiocarbamate (NABAM)
zinc-ethylene-1,2-bis-dithiocarbamate (ZINEB)
manganese-ethylene-1,2-bis-dithiocarbamate (polymeric)(MANEB)
tetramethylthiuramdisulphide (THIRAM)
1-oxy-3-acetyl-6-methyl-cyclohexene-(5)dione-(2,4) (DEHYDRO-ACETIC ACID)
8-hydroxyquinoline (8-QUINOLINOL)
2-dimethylamino-6-methyl-5-n-butyl-4-hydroxy-pyrimidine methyl-N-benzimidazole-2-yl-N-(butylcarbamoyl)carbamate (BENOMYL)
2-ethylamino-6-methyl-5n-butyl-4-hydroxypyrimidine
2,3-dicyano-1,4-dithia-anthraquinone (DITHIANON)
2-(4-thiazolyl)-benzimidazole
3,5-dimethyltetrahydro-1,3,5-thiadiazine-2-thione (DAZOMET)
2,3-dihydro-5-carboxanilido-6-methyl-1,4-oxathine pentachlorobenzyl alcohol.

Furthermore, the compounds of the formula I are suitable for combating plant pathogenic nematodes.

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
Dusts, tracking agents, granules, coated granules, impregnated granules and homogeneous granules.
Liquid forms:
a. active substances which are dispersible in water: wettable powders, pasts, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SIO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/ propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove in such a manner that, the size of the solid particles does not exceed 0.02 to 0.04 $\mu$ in wettable powders, and 0.03 $\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350°C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1 to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

a.

5 parts of active substance
95 parts of talcum b.

2 parts of active substance
1 part of highly disperse silicic acid
97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder:

The following constituents are used for the preparation of (a) a 40%, (b) and (c) a 25%, and (d) a 10% wettable powder:

a.

40 parts of active substance,
5 parts of sodium lignin sulphonate,
1 part of sodium dibutyl-naphthalene sulphonate,
54 parts of silicic acid.

b.

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin.

d.

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:

a.

10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene, b.

25 parts of active substance,
2.5 parts of epoxidised vegetable oil,
10 parts of an alkylarylsulphonate/fatty alcoholpolyglycol ether mixture
5 parts of dimethylformamide,
57.5 parts of xylene.

From these concentrates it is possible to produce, by dilution with water, emulsions of any desired concentration.

Spray:

The following constituents are used to prepare a 5% spray:

5 parts of active substance,
1 part of epichlorohydrin,
94 parts of benzine (boiling limits 160° – 190°C).

EXAMPLE 1

N-(2-methyl-4-chlorophenyl)-N'-methyl-N'-(2-methylphenoxycarbonyl)-formamidine.

To a solution of 54.8 g of N-(2-methyl-4-chlorophenyl)-N'-methyl-formamidine in 400 ml of dry benzene are added dropwise, while stirring, 25.5 g of chloroformic-o-tolyl ester, the temperature being kept between 5°–10°C. After the mixture has been stirred constantly for 12 hours at room temperature, the resulting hydrochloride salt of the formamidine used simultaneously as base is filtered off, washed with benzene, and the benzene solution evaporated in vacuo. Recrystallisation from methanol yields the product of the formula

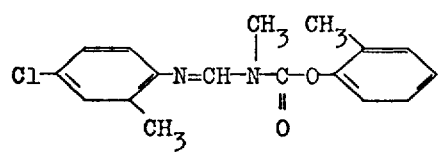

with a melting point of 68°–70°C.
The following compounds are manufactured in analogous manner:
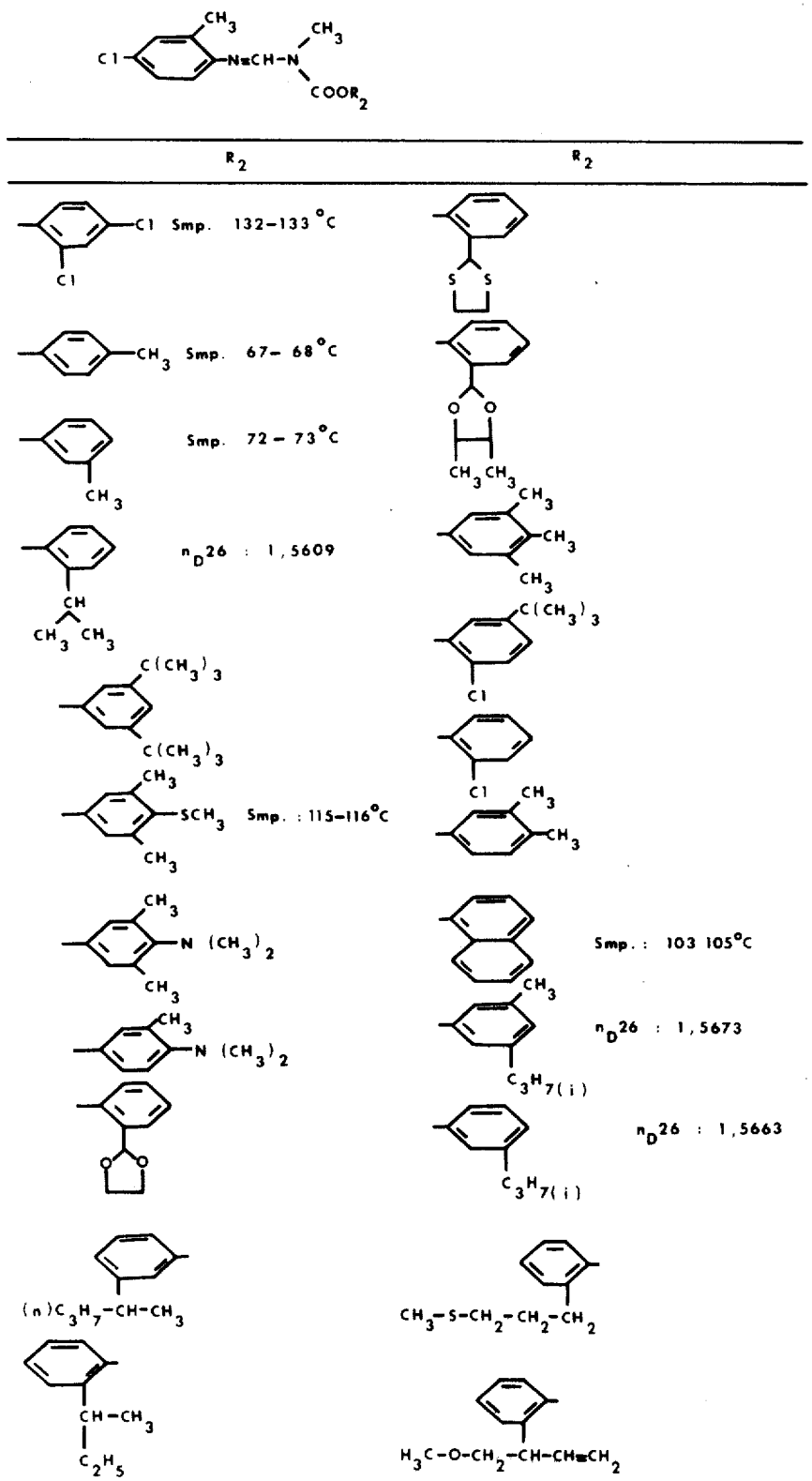

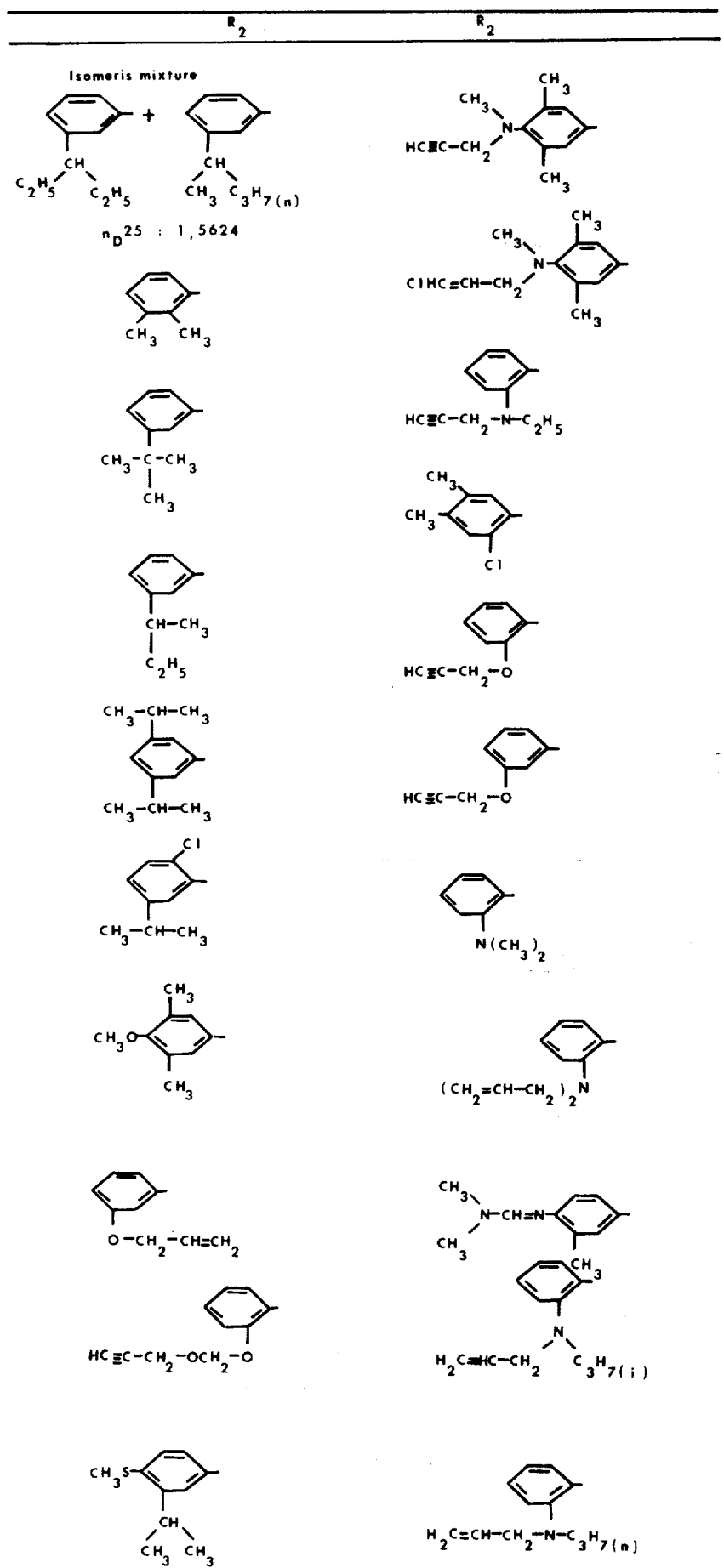

| $R_2$ | $R_2$ |
|---|---|
| 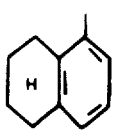 | 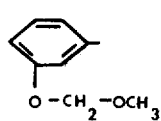 |
| 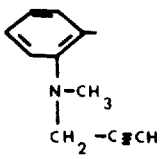 | 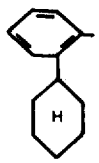 |
| 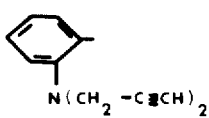 | 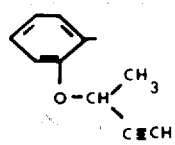 |
| 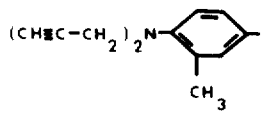 | 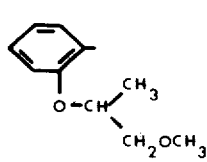 |
| 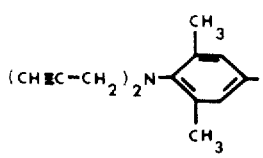 | |
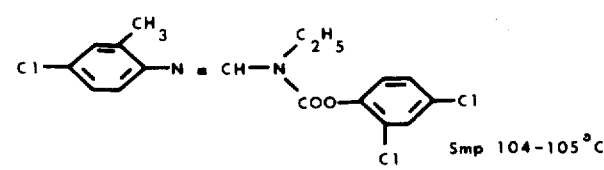
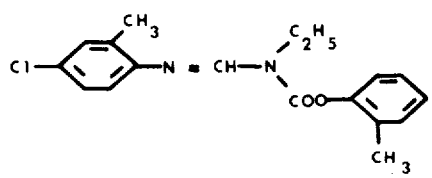
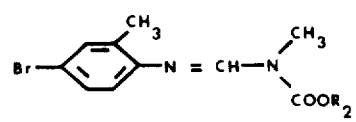
| $R_2$ | $R_2$ |
|---|---|
| 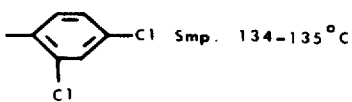 Smp. 134–135°C | 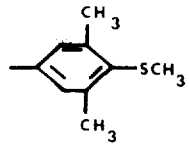 |

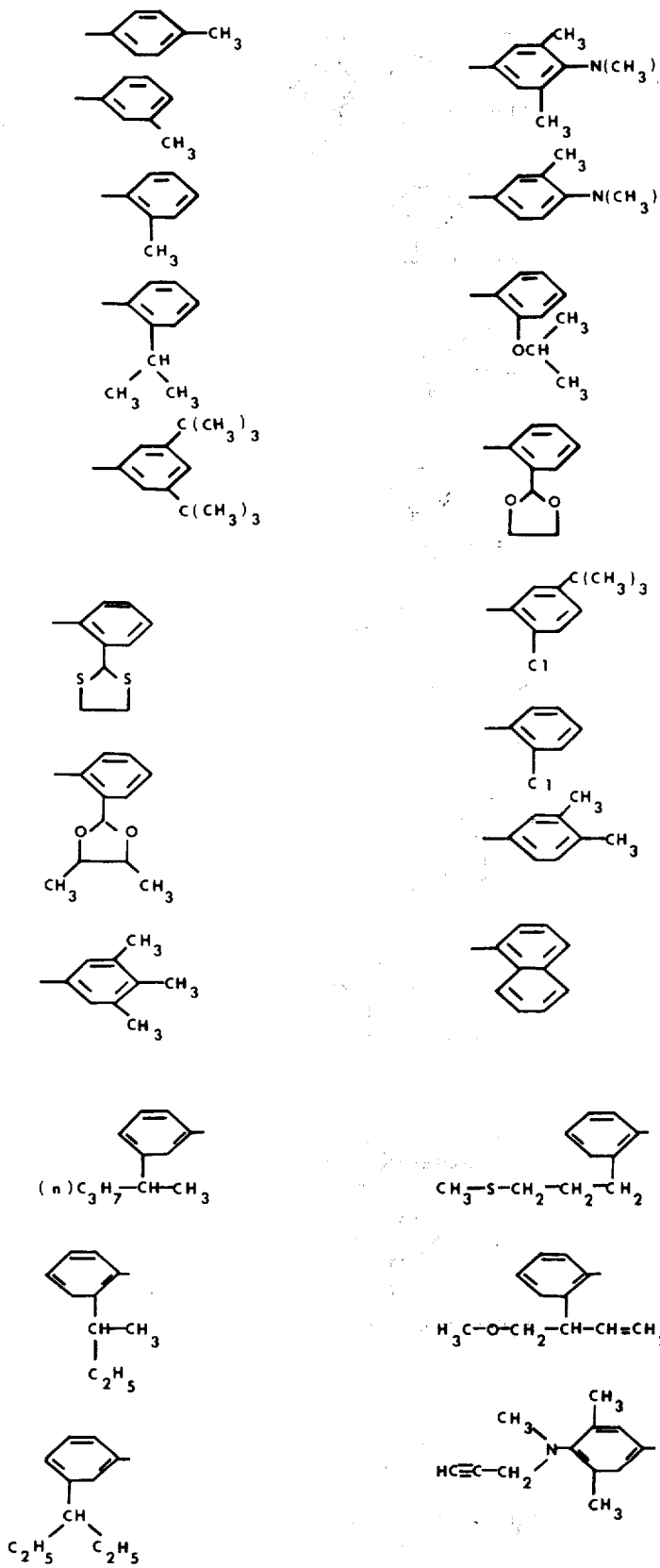

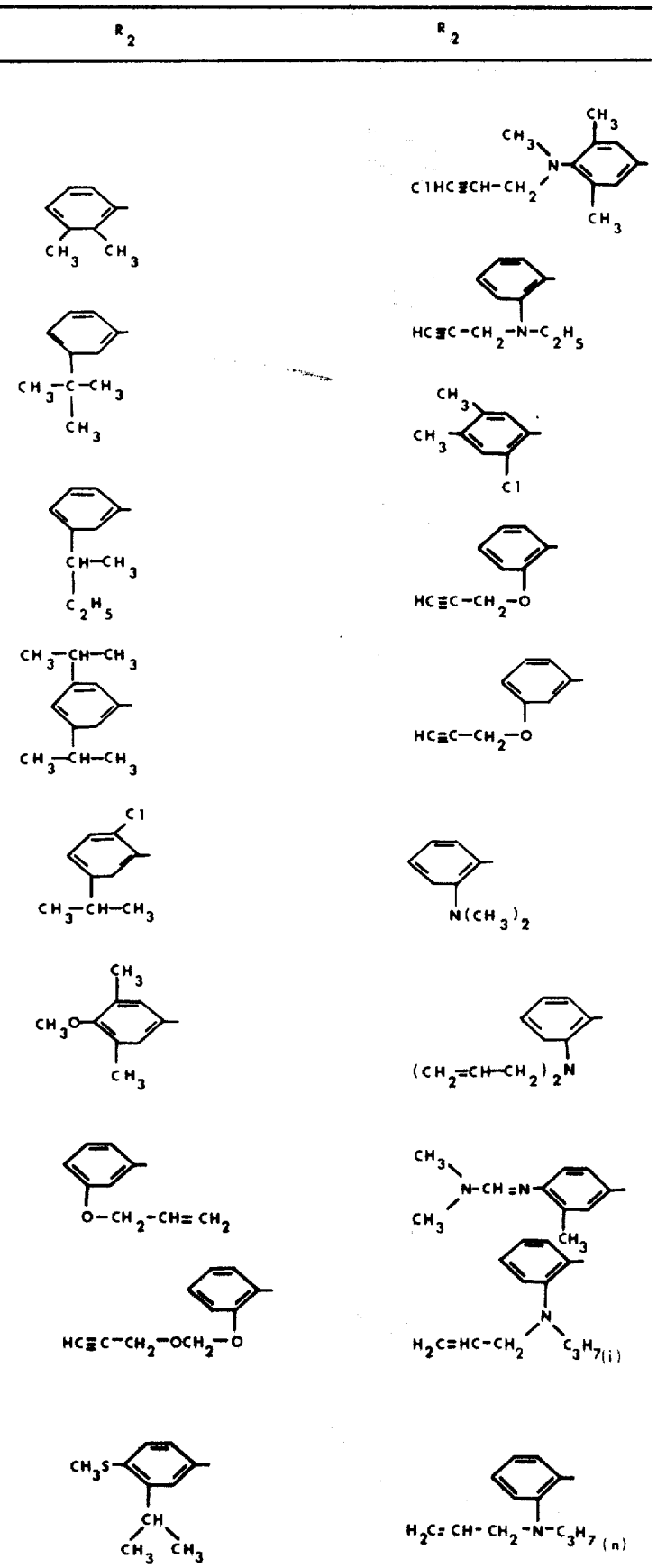

| $R_2$ | $R_2$ |
|---|---|
| 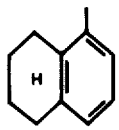 | 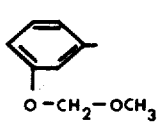 |
| 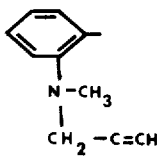 | 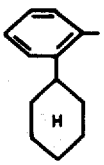 |
| 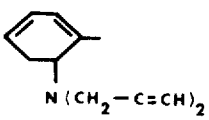 | 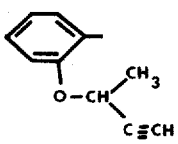 |
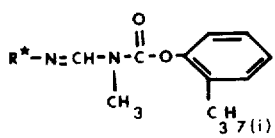
| $R^*$ | Physical Data | $R^*$ | Physical Data |
|---|---|---|---|
| 2-$C_3H_7(i)$-phenyl | $n_D^{25}$ : 1.5732 | phenyl | |
| 2,4-$(CH_3)_2$-phenyl | $n_D^{25}$ : 1.5642 | 4-$(i)C_3H_7$-phenyl | |
| | | 3-$CF_3$-phenyl | |
| 2,6-$(C_3H_7(i))_2$-phenyl | $n_D^{26}$ : 1.5407 | 2,4,6-$(CH_3)_3$-phenyl | |
| 2,6-$(CH_3)_2$-phenyl | $n_D^{26}$ : 1.5532 | 4-Cl-2-$C_2H_5$-phenyl | |
| 2,6-$(C_2H_5)_2$-phenyl | $n_D^{26}$ : 1.5462 | 4-Cl-2-$C_3H_7(i)$-phenyl | |
| 3-$CH_3$-phenyl | $n_D^{26}$ : 1.5685 | 3-F-phenyl | |
| 3-Cl-2-$CH_3$-phenyl | | 3,4-$Cl_2$-phenyl | |
| | | 2-$C_2H_5$-phenyl | |
| 4-$CH_3O$-phenyl | $n_D^{23}$ : 1.5674 | | |

| R* | Physical Data | R* | Physical Data |
|---|---|---|---|
| 2,4-dichlorophenyl (Cl, Cl) | Smp.: 99–100°C | o-tolyl (CH₃) | |
| 4-cyanophenyl (NC) | $n_D^{23}$: 1,5843 | 4-(n-C₄H₉)phenyl | |
| 4-(C₂H₅O-CO)phenyl | Smp.: 58–59°C | 4-(H₂C=CH-CH₂-O)phenyl | |
| o-tolyl (CH₃) | $n_D^{23}$: 1,5684 | 4-(HC≡C-CH₂-O)phenyl | |
| | | 4-(H₂C=CCl-CH₂-O)-2-methylphenyl | |

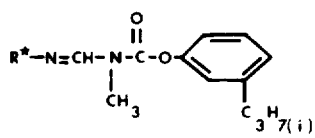

$$R^*-N=CH-\underset{\underset{CH_3}{|}}{N}-\overset{\overset{O}{\|}}{C}-O-\text{C}_6\text{H}_4-\text{C}_3\text{H}_7(i)$$

| R* | Physical Data | R* | Physical Data |
|---|---|---|---|
| 3,4-dimethylphenyl | $n_D^{25}$: 1,562 | 2-Cl-4-(i-C₃H₇)phenyl | |
| 2,6-diethylphenyl | $n_D^{26}$: 1,5474 | 2-fluorophenyl | |
| phenyl | $n_D^{26}$: 1,5780 | 3,4-dichlorophenyl | |
| 2-Cl-3-methylphenyl | $n_D^{23}$: 1,5608 | 2-Cl-4-(i-C₃H₇)phenyl | |
| 2,6-dimethylphenyl | $n_D^{25}$: 1,5630 | 2-fluorophenyl | |
| 4-chlorophenyl | $n_D^{26}$: 1,5769 | 3,4-dichlorophenyl | |
| 3-(i-C₃H₇)phenyl | $n_D^{26}$: 1,5583 | 2,4-dichlorophenyl | |
| 2,6-di(i-C₃H₇)phenyl | | 2-ethylphenyl | |
| | | o-tolyl | |
| | | 4-methoxyphenyl | |

| R* | Physical Data | R* | Physical Data |
|---|---|---|---|
| 2,3-dimethylphenyl | | 4-(n-C₄H₉)phenyl | |
| | | 4-NC-phenyl | |
| | | 4-(H₂C=CH-CH₂-O)phenyl | |
| 4-(i-C₃H₇)phenyl | | 4-(HC≡C-CH₂-O)phenyl | |
| 3-CF₃-phenyl | | 4-(H₂C=C(Cl)-CH₂-O)-2-CH₃-phenyl | |
| 2,4-dimethylphenyl | | | |
| 2-CH₃, 6-C₂H₅-phenyl | | 2-Cl, 3-CH₃-phenyl | $n_D^{26}: 1.5740$ |
| 2,6-Cl-phenyl | | | |

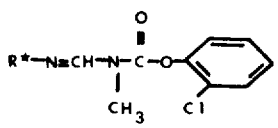

| R* | Physical Data | R* | Physical Data |
|---|---|---|---|
| 3-CH₃-phenyl | $n_D^{24}: 1.5910$ | 2-Cl, 6-C₂H₅-phenyl | |
| 2,6-(CH₃)₂-phenyl | $n_D^{26}: 1.5809$ | 2-Cl, 6-(i-C₃H₇)-phenyl | |
| 2-Cl, 6-CH₃-phenyl | Smp.: 57–59°C | 2-F-phenyl | |
| 4-Cl-phenyl | $n_D^{26}: 1.5935$ | 2,4-Cl₂-phenyl | |
| 2,6-(C₂H₅)₂-phenyl | $n_D^{25}: 1.5647$ | 2,3,4-Cl₃-phenyl | |
| 2-CH₃, 6-Cl-phenyl | $n_D^{26}: 1.5694$ | 2-C₂H₅-phenyl | |
| 2,4,6-(CH₃)₃-phenyl | $n_D^{25}: 1.5787$ | 2-CH₃-phenyl | |
| | | 4-CH₃O-phenyl | |
| phenyl | $n_D^{26}: 1.6101$ | 4-(n-C₄H₉)-phenyl | |

| R* | Physical Data | R* | Physical Data |
|---|---|---|---|
| 2-iPr-C₆H₄ | | 4-NC-C₆H₄ | |
| 2,6-(iPr)₂-C₆H₃ | | 4-(H₂C=CH-CH₂-O)-C₆H₄ | |
| 2,6-(CH₃)₂-C₆H₃ | | 4-(HC≡C-CH₂-O)-C₆H₄ | |
| 4-iPr-C₆H₄ | | 4-(H₂C=CCl-CH₂-O)-3-CH₃-C₆H₃ | |
| 3-CF₃-C₆H₄ | | | |
| 2,4-(CH₃)₂-C₆H₃ | | | |

$$R^*-N=CH-N(CH_3)-C(=O)-O-\text{naphthyl}$$

| R* | Physical Data | R* | Physical Data |
|---|---|---|---|
| 2,6-(CH₃)₂-C₆H₃ | $n_D^{26} : 1.6030$ | 2-F-C₆H₄ | |
| 2,6-(C₂H₅)₂-C₆H₃ | Smp.: 85–87°C | 3,4-Cl₂-C₆H₃ | |
| 2,4,6-(CH₃)₃-C₆H₂ | | 2,4,5-Cl₃-C₆H₂ | |
| 2-iPr-C₆H₄ | | 2-C₂H₅-C₆H₄ | |
| 2,6-(iPr)₂-C₆H₃ | | 2-CH₃-C₆H₄ | |
| C₆H₅ | | 4-CH₃O-C₆H₄ | |
| | | 4-(n)C₄H₉-C₆H₄ | |

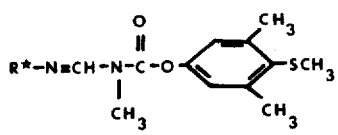

| R* | Physical Data | R* | Physical Data |
|---|---|---|---|
|  | | 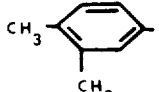 | |
| 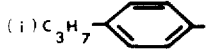 | | | |
| 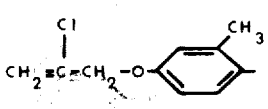 | | 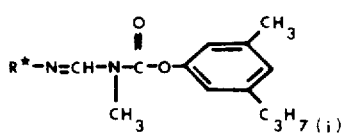 | |
|  | | | |
| R* | Physical Data | R* | Physical Data |
|---|---|---|---|
|  | $n_D^{25}$ : 1,5471 | 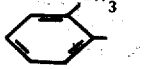 | |
| 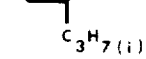 | $n_D^{26}$ : 1,5583 | 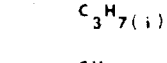 | |
| 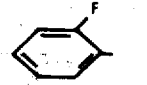 | $n_D^{23}$ : 1,5592 |  | |
|  | $n_D^{24}$ : 1,5472 | 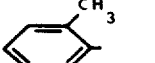 | |
| 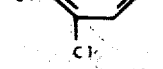 | $n_D^{26}$ : 1,5571 | 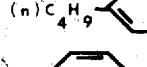 | |
| 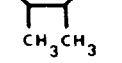 | |  | |
| 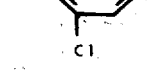 | | 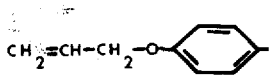 | |
| 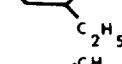 | | 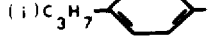 | |
| 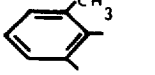 | | 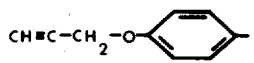 | |
| 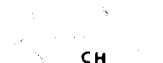 | |  | |
| 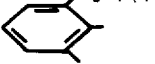 | |  | |

| R* | Physical Data | R* | Physical Data |
|---|---|---|---|
| 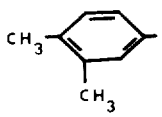 | |  | |
| 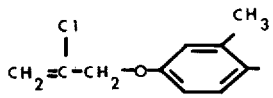 | | 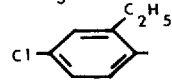 | |
|  | | | |
| 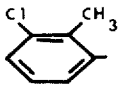 | | | |
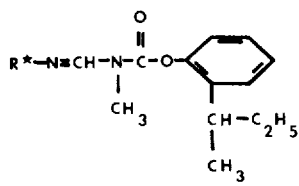
| R* | Physical Data | R* | Physical Data |
|---|---|---|---|
|  | $n_D^{26}$ :1,5666 | 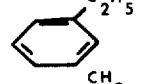 | |
| 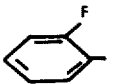 | $n_D^{26}$ :1,5694 |  | |
| 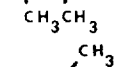 | $n_D^{26}$ :1,5447 | 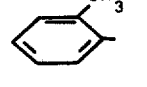 | |
| 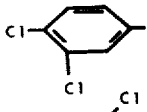 | $n_D^{25}$ : 1,5713 | 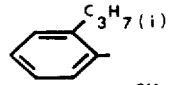 | |
|  | $n_D^{23}$ :1,5588 | 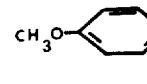 | |
| 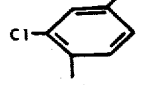 | | 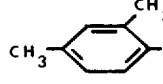 | |
| | | 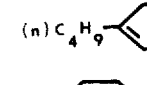 | |
| 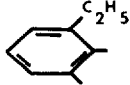 | | 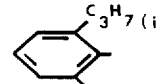 | |
| | | 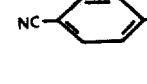 | |
| 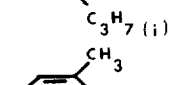 | | 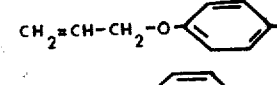 | |
| | | 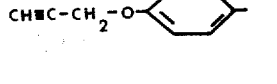 | |

| R* | Physical Data | R* | Physical Data |
|---|---|---|---|
A mixture of
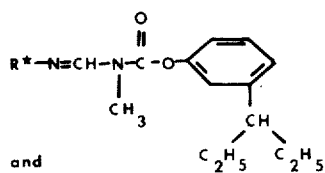
and
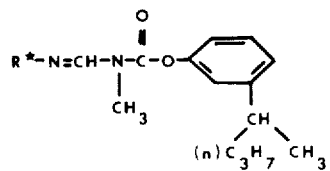
| R* | Physical Data | R* | Physical Data |
|---|---|---|---|
| | $n_D^{26}$ : 1,5636 | | |
| | $n_D^{26}$ : 1,5519 | | |
| | $n_D^{26}$ : 1,5524 | | |
| | $n_D^{25}$ : 1,5568 | | |
| | $n_D^{26}$ : 1,5566 | | |

| R* | Physical Data | R* | Physical Data |
|---|---|---|---|
| 2,6-(C₂H₅)₂-C₆H₃ | | 4-(CH₂=CH-CH₂-O)-C₆H₄ | |
| 4-(i-C₃H₇)-C₆H₄ | | 4-(CH≡C-CH₂-O)-C₆H₄ | |
| 3-CF₃-C₆H₄ | | 4-(CH₂=C(Cl)-CH₂-O)-C₆H₄ | |
| 2,6-(CH₃)₂-C₆H₃ | | 2-Cl-6-CH₃-C₆H₃ | |

$$R^*-N=CH-N(CH_3)-\overset{\overset{O}{\|}}{C}-O-C_6H_2(CH_3)_3\text{-3,4,5}$$

| R* | Physical Data | R* | Physical Data |
|---|---|---|---|
| 3,4-(CH₃)₂-C₆H₃ | $n_D^{26}$ : 1.5668 | 2,4-Cl₂-C₆H₃ | |
| 2-(i-C₃H₇)-C₆H₄ | | 2,4,6-Cl₃-C₆H₂ | |
| 2,6-(i-C₃H₇)₂-C₆H₃ | | 2-C₂H₅-C₆H₄ | |
| 2,6-(CH₃)₂-C₆H₃ | | 2-CH₃-C₆H₄ | |
| 2,6-(C₂H₅)₂-C₆H₃ | | 4-CH₃O-C₆H₄ | |
| C₆H₅ | | 4-(n-C₄H₉)-C₆H₄ | |
| 4-(i-C₃H₇)-C₆H₄ | | 4-NC-C₆H₄ | |
| 3-CF₃-C₆H₄ | | 4-(CH₂=CH-CH₂-O)-C₆H₄ | |
| 2,6-(CH₃)₂-C₆H₃ | | 4-(CH≡C-CH₂-O)-C₆H₄ | |
| | | 3-CH₃-4-(CH₂=C(Cl)-CH₂-O)-C₆H₃ | |
| | | 2-Cl-6-CH₃-C₆H₃ | |

| R* | Physical Data | R* | Physical Data |
|---|---|---|---|
| 4-Cl, 2-C₂H₅-C₆H₃ | | | |
| 4-Cl, 2-CH(CH₃)₂-C₆H₃ | | | |
| 2-F-C₆H₄ | | | |
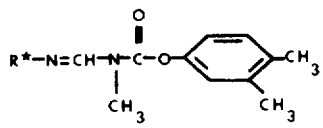
| R* | Physical Data | R* | Physical Data |
|---|---|---|---|
| 2,6-(C₂H₅)₂-C₆H₃ | | | |
| 2,4,5-(CH₃)₃-C₆H₂ | $n_D^{24}$ : 1,5739 | | |
| 2-C₃H₇(i)-C₆H₄ | | | |
| 2,6-(C₃H₇(i))₂-C₆H₃ | | | |
| 2,6-(CH₃)₂-C₆H₃ | | | |
| C₆H₅ | | 2-F-C₆H₄ | |
| 4-C₃H₇(i)-C₆H₄ | | 2,3-Cl₂-C₆H₃ | |
| 3-CF₃-C₆H₄ | | 2,4,5-Cl₃-C₆H₂ | |
| 3,5-(CH₃)₂-C₆H₃ | | 2-C₂H₅-C₆H₄ | |
| | | 2-CH₃-C₆H₄ | |

| R* | Physical Data | R* | Physical Data |
|---|---|---|---|
| 4-Cl-2-C₂H₅-C₆H₃- | | 4-CH₃O-C₆H₄- | |
| 4-Cl-2-(CH(CH₃)₂)-C₆H₃- | | 4-(n-C₄H₉)-C₆H₄- | |
| | | 4-NC-C₆H₄- | |
| | | 4-(CH₂=CH-CH₂-O)-C₆H₄- | |
| | | 4-(CH≡C-CH₂-O)-C₆H₄- | |
| | | 4-(CH₂=CCl-CH₂-O)-3-CH₃-C₆H₃- | |
| | | 2-Cl-3-CH₃-C₆H₃- | |
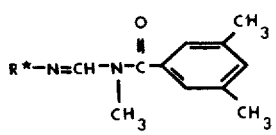
| R* | Physical Data | R* | Physical Data |
|---|---|---|---|
| 2,6-(C₂H₅)₂-C₆H₃- | $n_D^{25}$ : 1,5521 | 2,3-(CH₃)₂-C₆H₃- | |
| 2,6-(CH₃)₂-C₆H₃- | | 4-Cl-2-C₂H₅-C₆H₃- | |
| 2-(i-C₃H₇)-C₆H₄- | | 4-Cl-2-(CH(CH₃)₂)-C₆H₃- | |
| | | 2-F-C₆H₄- | |
| 2,6-(i-C₃H₇)₂-C₆H₃- | | 3-Cl-C₆H₄- | |
| 2,6-(CH₃)₂-C₆H₃- | | 2,4,5-Cl₃-C₆H₂- | |
| C₆H₅- | | 2-C₂H₅-C₆H₄- | |
| 4-(i-C₃H₇)-C₆H₄- | | 2-CH₃-C₆H₄- | |
| | | 4-CH₃O-C₆H₄- | |
| 3-CF₃-C₆H₄- | | 4-(n-C₄H₉)-C₆H₄- | |

| R* | Physical Data | R* | Physical Data |
|---|---|---|---|
|  | | | |
|  | | | |
|  | | | |
|  | | | |
|  | | | |
| R* | Physical Data | R* | Physical Data |
|---|---|---|---|
|  | $n_D^{23}$ :1,5479 | | |
|  | | | |
|  | | | |
|  | | | |
|  | |  | |
|  | |  | |
|  | |  | |
|  | |  | |
|  | |  | |
|  | |  | |

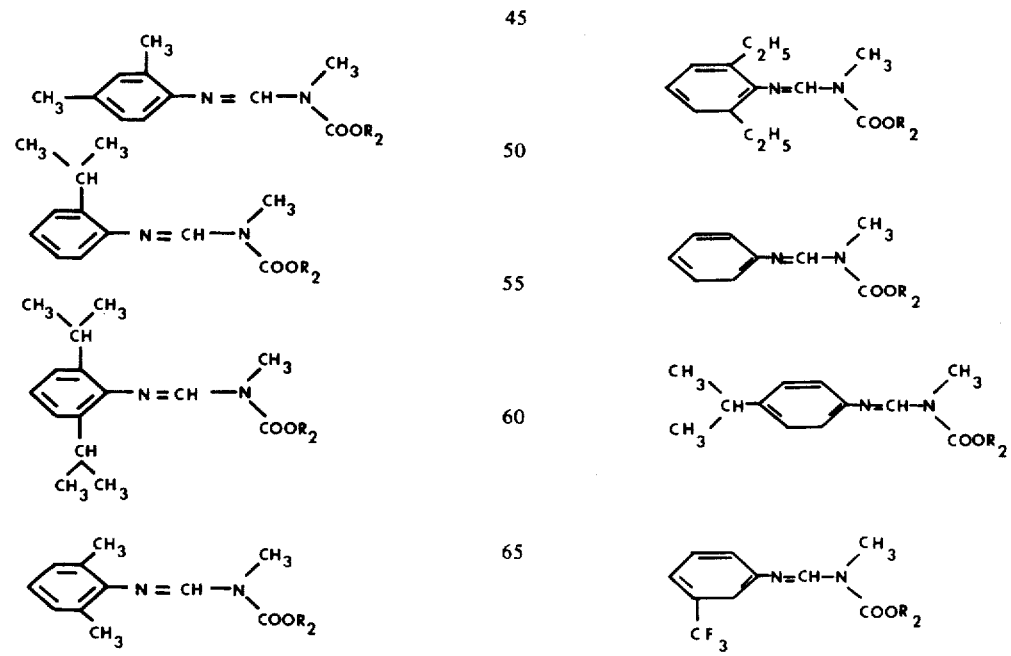

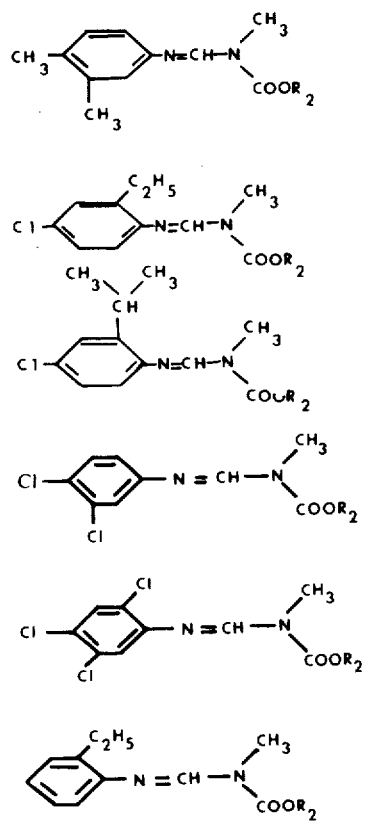
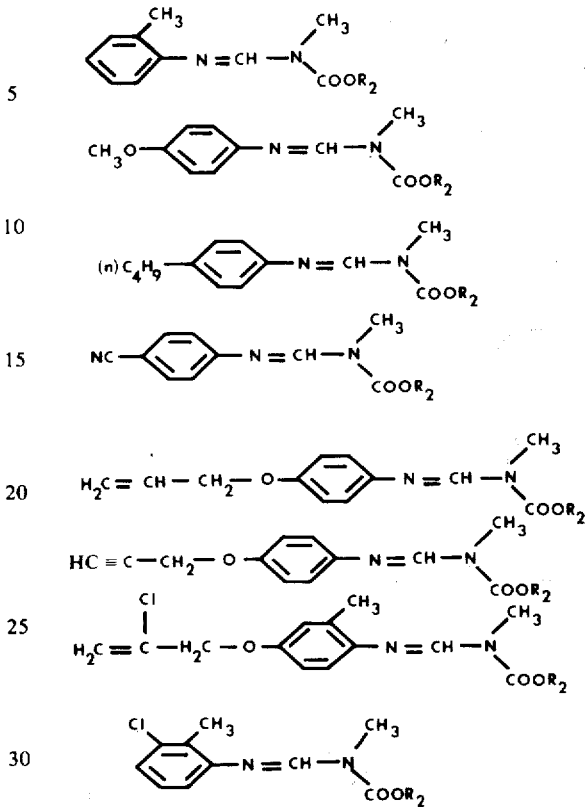
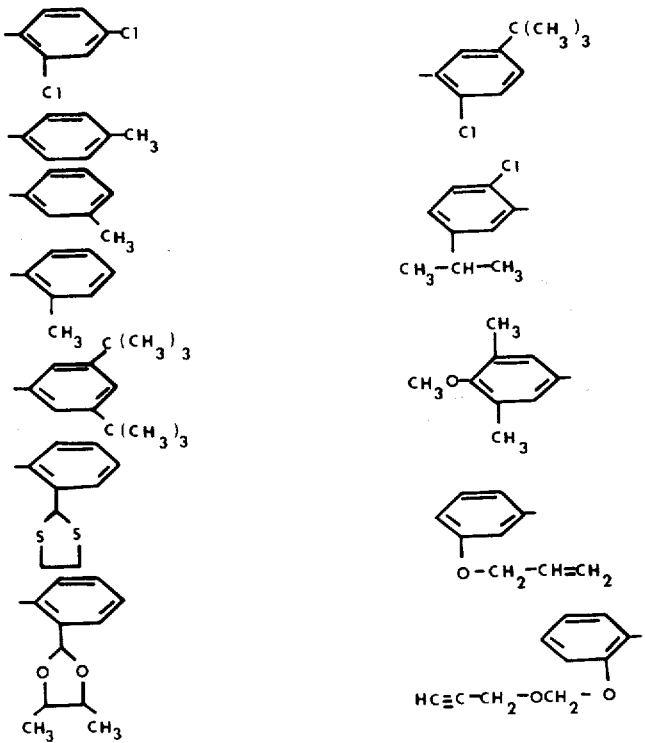

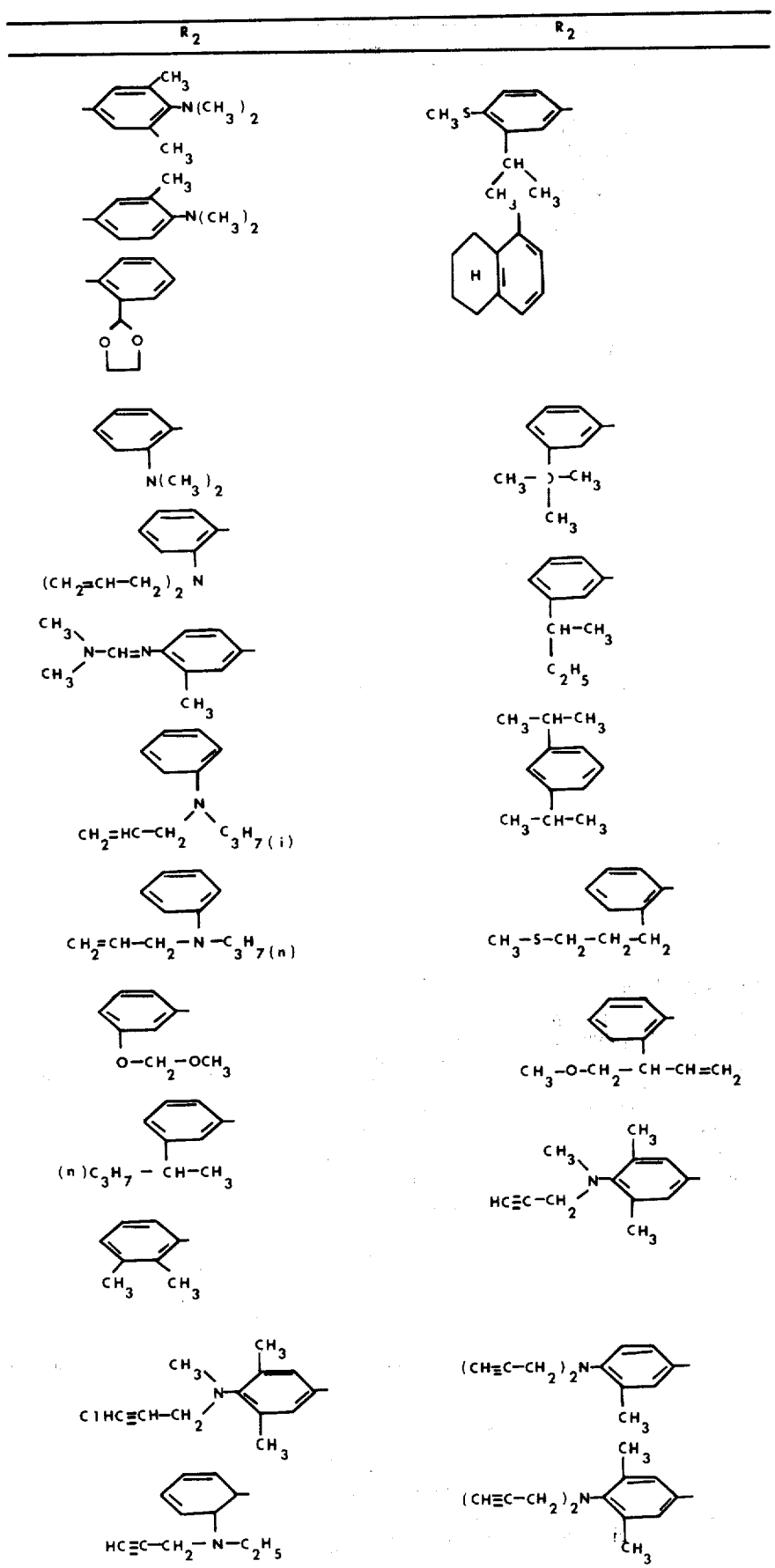

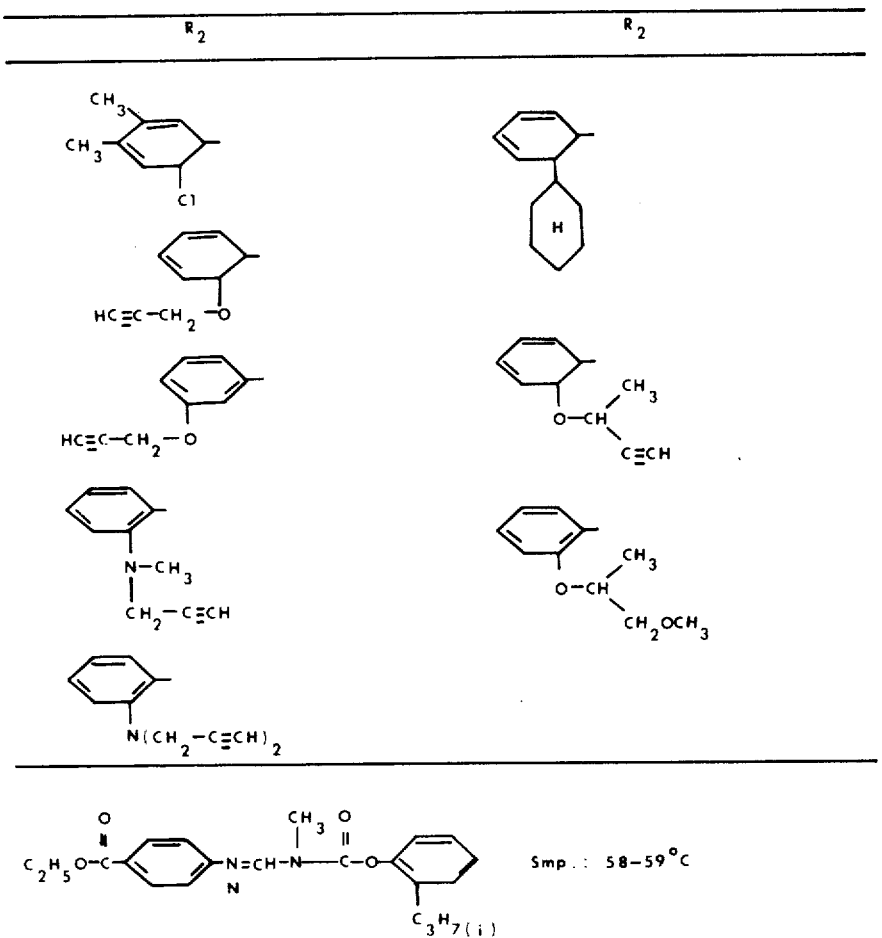

EXAMPLE 2

A. Insecticidal ingest poison action

Tobacco and potato plants were sprayed with a 0.05% aqueous emulsion (obtained from a 10% emulsifiable concentrate).

After the coating had dried, the tobacco plants were populated with Egyptian cotton leaf worms (*Spodoptera littoraralis*) and the potato plants with Colorado potato beetle larvae (*Leptinotarsa decemlineata*). The test was carried out at 24°C and 60% relative humidity. In the above test, the compounds according to Example 1 displayed good ingest poison action against *Spodoptera littoralis* and *Leptinotarsa decemlineata*.

B. Systemic insecticidal action

To determine the systemic action, rooted bean plants (*Vicia fabae*) were put into a 0.01% aqueous active substance solution (obtained from a 10% emulsifiable concentrate). After 24 hours, aphids (*Aphis fabae*) were placed on the parts of the plant above the soil. The aphids were protected from contact and gas action by means of a special device. The test was carried out at 24°C and 70% relative humidity. In the above tests the compounds according to Example I displayed good insecticidal ingest poison and systemic insecticidal action.

EXAMPLE 3

Action against *Chilo suppresalis*

Six rice plants at a time of the variety Caloro' were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rate of application: 8 kg of active substance per hectare). Evaluation of the insecticidal action took place 10 days after application of the granules.

The compounds according to Example 1 were active in the above test against *Chilo suppressalis*.

EXAMPLE 4

Action against soil insects

Sterilised compost earth was homogeneously mixed with a wettable powder containing 25% of active substance so that there resulted a rate of application of 8 kg of active substance per hectare.

Young zucchetti plants (*Cucumis pepo*) were put into plastic pots with the treated soil (3plants per pot; diameter of pot = 7 cm). Each pot was infected immediately afterwards with 5 *Aulacophora femoralis* and Pachmoda or Chortophila larvae. The control was carried out 4, 8, 16 and 32 days after depositing the larvae.

At 80–100% kill after the first control, a fresh infestation with 5 larvae each was carried out in the same soil sample with 3 new zucchetti plants. If the activity was less than 80%, the remaining larvae remained in the soil sample until the control immediatedly following. If an active substance at a rate of application of 8 kg/ha still effected a 100% kill, a further control with 4 and 2 kg of active substance per hectare was carried out.

In the above test, the compounds according to Example 1 displayed action against *Aulacophora fermoralis*, *Pachmoda* and *Chortophila* larvae.

EXAMPLE 5

Action against ticks

A. *Rhicephalus bursa*

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be adsorbed by the cotton wool.

In the case of the adults evaluation took place after 2 weeks, and in that of the larvae after 2 days. Each test was repeated twice.

B. *Boophilus microplus* (larvae)

Tests were carried out in each case with 20 OP-sensitive larvae using an analogous dilution series as in the case of test A. (The resistence refers to the tolerability of Diazinon).

The compounds according to Example 1 acted in these tests against adults and larvae of *Rhicephalus bursa* sensitive and OP-resistent larvae of *Boophilus microplus*.

EXAMPLE 6

Acaracidal action

*Phaseolus vulgaris* (dwarf beans) have an infested piece of leaf from a mass culture of *Tetranychus urticae* placed on them 12 hours before the test for the acaricidal action. The mobile stages which have migrated are sprayed with the emulsified test preparations from a chromatography atomiser so that the spray broth does not run off. The number of living and dead larvae, adults and eggs are evaluated after 2 to 7 days under a stereoscopic microscope. During the "interim", the treated plants are kept in greenhouse compartments at 25°C.

The compounds according to Example 1 were active in the above test against eggs, larvae and adults of *Tetranychus urticae*.

EXAMPLE 7

Action against soil nematodes

To test the action against soil nematodes, the active substance (in the concentration indicated in each case is applied to and intimately mixed with soil infected with root gall nematodes (*Meloidgyne Avenaria*). Immediately afterwards, tomato cuttings are planted in the thus prepared soil in a series of tests and after a waiting time of 8 days tomato seeds are sown in another test series.

In order to assess the nematocidal action, the galls present on the roots are counted 28 days after planting and sowing respectively. In this test the compounds according to Example 1 display good action against *Meloidgyne Avenaria*.

We claim:
1. A compound of the formula

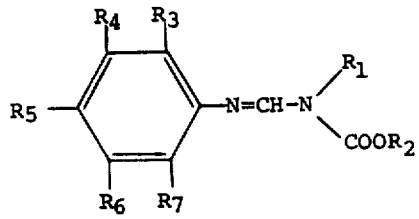

wherein $R_1$ represents hydrogen, $C_1$-$C_4$ alkyl, $C_3$-$C_5$ alkenyl or $C_3$-$C_5$ alkynyl, $R_2$ represents α-naphthyl, or phenyl substituted by halogen, $C_1$-$C_5$ alkyl, $C_1$-$C_4$ haloalkyl, $C_1$-$C_4$ alkoxy, alkoxyalkyl having 1 to 4 carbon atoms in each of the alkyl moieties, $C_1$-$C_4$ alkylthio, $C_3$-$C_4$ alkynyloxy, dialkylamino having $C_1$-$C_4$ alkyl groups, dialkenylamino having $C_3$-$C_4$ alkenyl groups, dialkynylamino having $C_3$C_4$ alkynyl groups, N-lower alkyl-N-($C_3$-$C_4$)alkynylamino, N-lower alkyl-N-($C_3$-$C_4$)alkenylamino, OH, CN, $NO_2$, cyclopentyl, monomethylaminomethyleneimino, dimethylaminomethyleneimino, 1,3-dioxolan, 1,3-dithiolan, and 4,5-dimethyl-1,3-dioxolan wherein the phenyl group is not substituted simultaneously in the 2-position by a methyl group and in the 4-position by a chlorine atom, and $R_3$, $R_4$, $R_5$, $R_6$ and $R_7$ represent one or more radicals which are the same or different, selected from hydrogen, halogen atoms or $C_1$-$C_4$ alkyl, $C_1$-$C_4$ alkoxy, $C_1$-$C_4$ alkylthio, $C_3$-$C_5$ alkenyloxy, $C_3$-$C_5$ alkynyloxy, $CF_3$, or nitro groups.

2. A compound according to claim 1, wherein $R_1$ represents methyl, $R_2$ represents α-naphthyl, 2-methylphenyl, 3-methylphenyl, 2-chlorophenyl, 2-isopropylphenyl, 3-isopropylphenyl, 3-methyl-5-isopropylphenyl, 2-chloro-5-tert.butylphenyl, 3,4-dimethylphenyl, 3,4,5-trimethylphenyl, 3,5-dimethyl-4-methylthiophenyl, 3,5-di-tert.butylphenyl, 2-isopropoxyphenyl, 3-methyl-4-dimethyl-aminophenyl, 3,5-dimethyl-4-dimethylaminophenyl, 3,5-dimethyl-4-diallylaminophenyl, 1,3-dioxolan-2-yl-phenyl, 1,3-dithiolan-2-yl-phenyl, (4,5-dimethyl-1,3-dioxolan-2-yl)-phenyl, 3-(1-methylbutyl)-phenyl, 2-sec.butylphenyl, 3-(1-ethylpropyl)-phenyl, 2,3-xylyl, 3-tert.butylphenyl, 3-sec.butylphenyl, 3,5-diisopropylphenyl, 2-chloro-5-isopropylphenyl, 3,5-dimethyl-4-methoxyphenyl, 4-(methyl-propargylamino)-3,5-xylyl, [4-(methyl-α-chloroallylamino)-3,5-xylyl,]2-(ethyl-propargylamino)phenyl, 2-chloro-4,5-dimethylphenyl, 2-(2-propynyloxy)-phenyl, 3-(2-propynyloxy)-phenyl, 2-dimethylaminophenyl, 2-diallylaminophenyl, 3-methyl-4-dimethylaminomethyleneiminophenyl, 3-dimethylaminomethyleneiminophenyl, 3-isopropyl-4-methylthiophenyl, 2-(methylpropargylamino)-phenyl, 2-(dipropargylamino)-phenyl, 4-(dipropargylamino)-3-tolyl, 4-(dipropargylamino)-3,5-xylyl, 2-(allylisopropylamino)-phenyl, 3-(allyl-isopropylamino)-phenyl, 3-methoxymethoxyphenyl, 2-cyclopentylphenyl, 2-(1-butyn-3-yl-oxy)-phenyl or 2-(1-methoxy-2-propoxy)-phenyl, and $R_3$, $R_4$, $R_5$, $R_6$, $R_7$ represent radicals which are the same or different, selected from hydrogen, fluorine, chlorine or bromine atoms, or methyl, methoxy, methylthio, trifluoroethyl, ethylpropyl, isopropyl, n-butyl, allyloxy, propargyloxy or O₂N groups.

3. Compounds according to claim 2 of the formulae

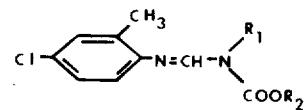
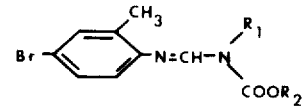
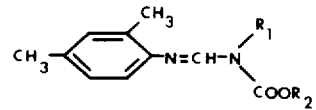
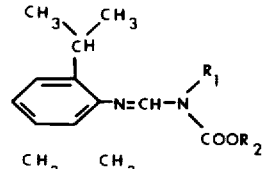
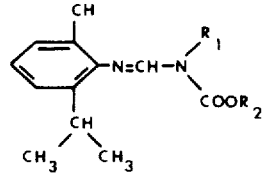
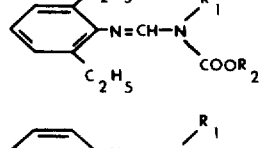
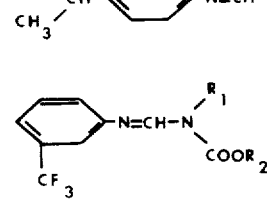
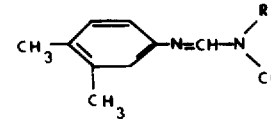
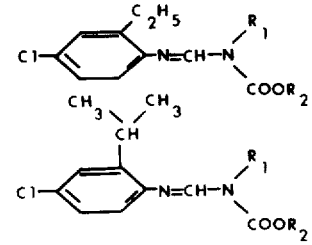

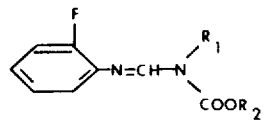
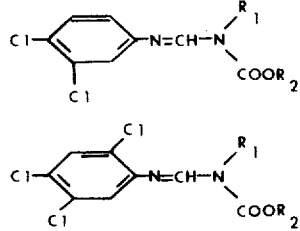
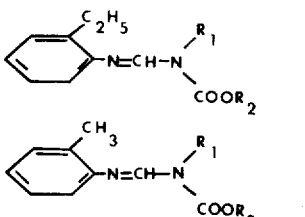
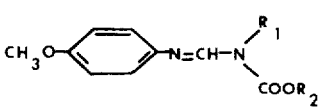
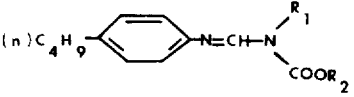
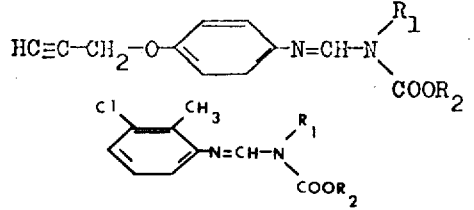

wherein
R₁ represents methyl, and
R₂ has the same meaning as in claim 2.

4. A compound according to claim 3 of the formula

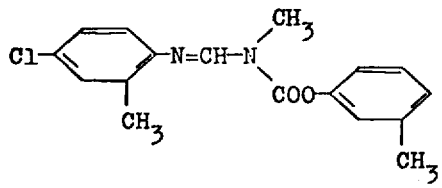

5. A compound according to claim 3 of the formula

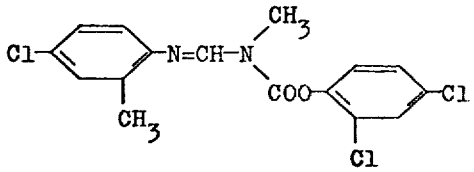

6. A compound according to claim 3 of the formula

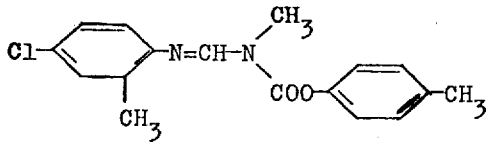

* * * * *

UNITED STATES PATENT AND TRADEMARK OFFICE
CERTIFICATE OF CORRECTION

PATENT NO. : 3,941,829
DATED : March 2, 1976
INVENTOR(S) : Georg Pissiotas and Dieter Duerr It is certified that error appears in the above-identified patent and that said Letters Patent are hereby corrected as shown below:

Column 63, Claim 2, line 3, change "trifluoroethyl" to

-- trifluoromethyl --.

Signed and Sealed this

Nineteenth Day of October 1976

[SEAL]

Attest:

RUTH C. MASON
Attesting Officer

C. MARSHALL DANN
Commissioner of Patents and Trademarks